United States Patent [19]

Noble et al.

[11] Patent Number: 5,561,516

[45] Date of Patent: Oct. 1, 1996

[54] CASINGLESS DOWN-HOLE FOR SEALING AN ABLATION VOLUME AND OBTAINING A SAMPLE FOR ANALYSIS

[75] Inventors: Donald T. Noble; Steven D. Braymen; Marvin S. Anderson, all of Ames, Iowa

[73] Assignee: Iowa State University Research Foundation, Inc., Ames, Iowa

[21] Appl. No.: 283,079

[22] Filed: Jul. 29, 1994

[51] Int. Cl.$^6$ .................................................... G01N 1/00
[52] U.S. Cl. ............................ 356/36; 250/253; 250/255; 250/269.1
[58] Field of Search ................................. 356/315–316, 356/318–319, 36, 440; 250/253–270, 269.1–269.8

[56] References Cited

U.S. PATENT DOCUMENTS

| | | | |
|---|---|---|---|
| 2,632,801 | 3/1953 | Donaldson | 250/256 |
| 2,935,615 | 5/1960 | True | 250/268 |
| 3,755,126 | 8/1973 | Misener et al. | 204/423 |
| 4,349,736 | 9/1982 | Miller | 250/269.1 |
| 4,587,422 | 5/1986 | Bowers | 250/256 |
| 4,598,577 | 7/1986 | Jowitt et al. | 356/36 |
| 5,166,747 | 11/1992 | Schroeder et al. | 250/256 X |

*Primary Examiner*—K. Hantis

*Attorney, Agent, or Firm*—Schwegman, Lundberg, Woessner & Kluth, P.A.

[57] ABSTRACT

A casing-less down hole sampling system for acquiring a subsurface sample for analysis using an inductively coupled plasma system is disclosed. The system includes a probe which is pushed into the formation to be analyzed using a hydraulic ram system. The probe includes a detachable tip member which has a soil point mad a barb, with the soil point aiding the penetration of the earth, and the barb causing the tip member to disengage from the probe and remain in the formation when the probe is pulled up. The probe is forced into the formation to be tested, and then pulled up slightly, to disengage the tip member and expose a column of the subsurface formation to be tested. An instrumentation tube mounted in the probe is then extended outward from the probe to longitudinally extend into the exposed column. A balloon seal mounted on the end of the instrumentation tube allows the bottom of the column to be sealed. A source of laser radiation is emitted from the instrumentation tube to ablate a sample from the exposed column. The instrumentation tube can be rotated in the probe to sweep the laser source across the surface of the exposed column. An aerosol transport system carries the ablated sample from the probe to the surface for testing in an inductively coupled plasma system. By testing at various levels in the down-hole as the probe is extracted from the soil, a profile of the subsurface formation may be obtained.

13 Claims, 5 Drawing Sheets

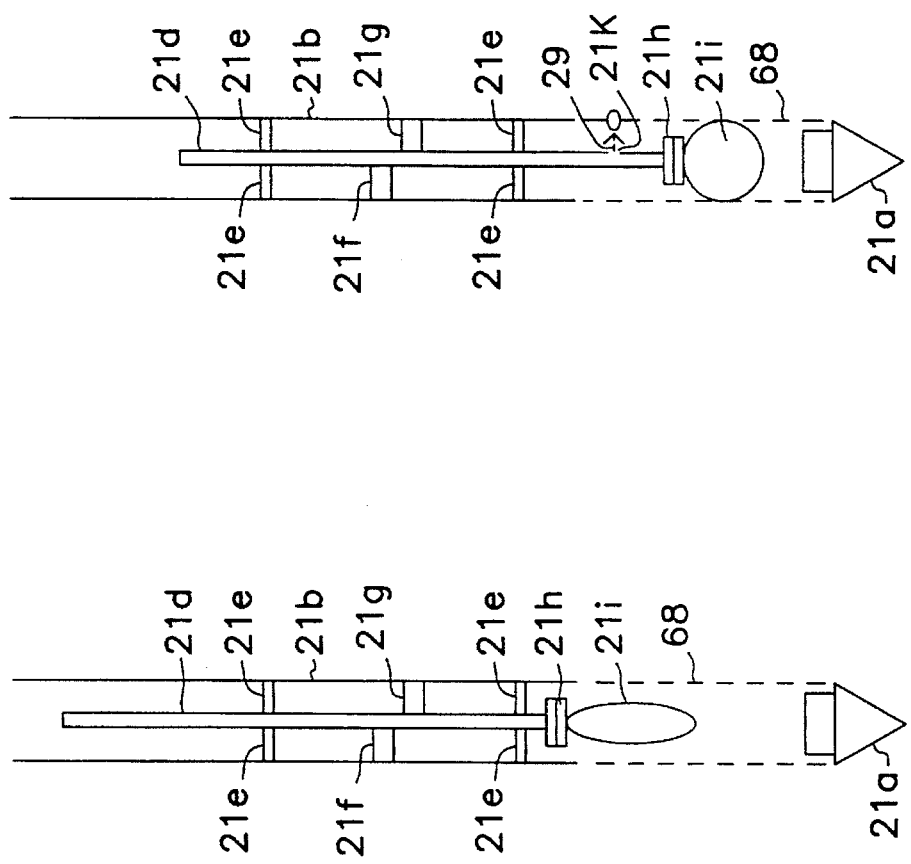

1

CASINGLESS DOWN-HOLE FOR SEALING AN ABLATION VOLUME AND OBTAINING A SAMPLE FOR ANALYSIS

STATEMENT OF GOVERNMENT RIGHTS

This invention was made with Government support under United States Department of Energy Contract No. W-7405-ENG-82. The Government has certain rights in the invention.

TECHNICAL FIELD OF THE INVENTION

This invention pertains generally to the field of material analysis and mineral exploration and assay, and particularly to method and apparatus for acquisition of a material sample from a subsurface formation and subsequent analysis of the sample.

BACKGROUND OF THE INVENTION

There is often the need for sampling and analysis of dangerous or hazardous materials, or materials located in hazardous environments. Examples include sampling and analyzing the condition of soil or water for the presence of hazardous waste such as radioactive waste or toxic chemicals. In addition, there is a demand for equipment and methods for mineral exploration and assay.

U.S. patent application Ser. No. 08/117,242, filed on Sep. 3, 1993, entitled Mobile Inductively Coupled Plasma System, describes a method and apparatus for sampling and analyzing hazardous materials proximate the site such that an absolute minimum of hazardous material need be released or removed from the site. According to one embodiment of the invention, a remotely controlled cart with a three-axis robot arm carries a probe which can be lowered into a sampling bore. The sampling probe includes a pair of inflatable annular seals used to enclose a volume of gas in the bore hole. The probe further includes laser ablation apparatus for ablating a sample from the subsurface formation, which is transported in an aerosol system to an inductively coupled plasma device for atomic elemental analysis. The system contemplates that the down-hole or bore is drilled and/or formed with a casing which includes one or more openings through which the probe may access the soil or subsurface formation to be sampled. While such casings can achieve depths of 150-200 feet, it is believed most subsurface areas of interest are much shallower, perhaps on the order of 50 feet or less. Accordingly, it would be deskable if there existed a less expensive and faster way to access subsurface formations with a sampling probe.

SUMMARY OF THE INVENTION

The present invention provides a system and method allowing for the elimination of the down-hole casing when obtaining samples for analysis in a system such as that described in U.S. application Ser. No. 08/117,242, described above, the disclosure of which is hereby incorporated by reference herein.

According to the invention, a probe having a small diameter housing substantially in the range of 1.5 inches to 3 inches is hydraulically pushed to the desired depth. While the depths achievable with this approach are limited, there is no percussion impact (as with percussion driven casings) or effect on instrumentation mounted in the probe. The tube probe includes a detachable tip member having a sand or soil point and a barb structure to prevent it from being withdrawn from the down-hole. When the desired depth is reached, the housing is withdrawn a short distance, detaching the tip member and leaving it at the bottom of the hole that has been formed by the passage of the housing and tip member. The probe includes an instrumentation tube for sealing an ablation volume and for sweeping a laser energy source across an area of the subsurface formation. The instrumentation tube may be moved incrementally up or down to obtain fresh samples from the subsurface formation if additional material is needed for analysis.

BRIEF DESCRIPTION OF THE DRAWINGS

FIG. 5A is a simplified schematic diagram of a probe according to the present invention prior to deployment of the seal;

FIG. 5B is a simplified schematic diagram of a probe according to the present invention with the seal inflated in position to collect a sample.

DETAILED DESCRIPTION OF THE INVENTION

Figure 1:
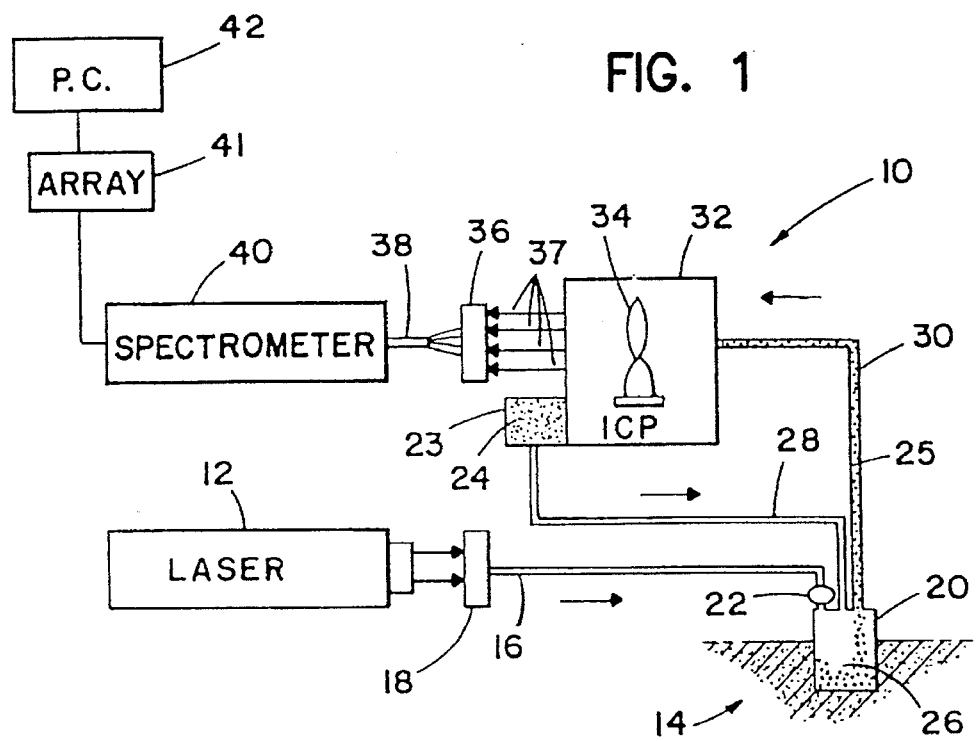
FIG. 1 is a simplified schematic illustration of an inductively coupled plasma testing system according to the present invention.

FIG. 1 is a simplified schematic illustration of a mobile inductively coupled plasma testing system 10 according to the present invention. Laser radiation from a laser 12 is directed to the sampling site 14 through fused silica fiber 16. According to one exemplary embodiment, the laser provides continuous or pulsed, fixed wavelength laser radiation at at least three different wavelengths: 1064 nm, 532 nm, and 355 nm. These wavelengths are chosen to provide a range of energies, as materials to be analyzed have different absorption characteristics at different wavelengths. Since current optical fibers are subject to damage at wavelengths below 350 nm and power levels of $10^8$ watts/cm$^2$/sec., it is best to utilize laser wavelengths above 350 nm. These constraints will change with the availability of better optical fibers. As most materials absorb optical radiation in the ultraviolet, ablation is more efficiently carded out at wavelengths below 400 nm. The lumonics dye laser (Hyper-Dye 300) pump by the Lambda Physik Excimer laser (Model EMG102MSC) is known to provide laser beams suitable for use in the system of the present invention. However, the preferred system for field operation is a solid state YAG laser.

A laser focusing system 18 is provided to focus the laser output onto the optical fiber 16, without overloading it. C Technologies fiber optics cable Model SRA-6-1-20-01 is known to be suitable for carrying the laser radiation to a probe 20, provided no more than $10^8$ watts/cm$^2$/sec. is applied to the head end of the fiber. As noted above, power levels in excess of this can damage the fiber. Focusing system 18 may include a filter to narrow the laser beam and reduce the power actually received by the optical fiber and a series of lenses to focus the laser radiation onto the end of the optical fiber. In the system of FIG. 1, the probe 20 (shown in more detail in FIGS. 4, 4B, 5A, 5B and 6) has optics 22 for focusing the laser radiation from the fiber 16 on the material to be sampled. The homing 21b of probe 20 is preferable constructed of steel or steel alloy, but other materials may be preferably to contend with different environmental conditions. The homing 21b is preferably substantially in the range of 1.5 inches to 3 inches, so as to permit the probe to be pushed into the soil. An argon gas source 23 supplies argon gas 24 to a probe sampling chamber 26 through an input line 28. The material ablated or sampled 25 by the laser radiation mixes with the argon 24 to form an aerosol which is drawn from the probe sampling chamber 26 through the aerosol output line 30 to the inductively coupled plasma (ICP) source 32. Argon 24 is also the support gas for the ICP 32. The present invention deploys an RF Plasma Products inductively coupled argon plasma system.

As is conventional in the art, the aerosol is directed into the plasma source 34 through an input line (not shown) to the ICP 32. The energized sample particles are excited to provide characteristic optical reduction of the elemental constituents of the sample 25 in the form of electromagnetic radiation 37, which is focused by a lens 36 and thereby subsequently channeled through an ICP output optical cable 38 to a remotely located multi-channel or sequential optical spectrometer 40. To carry the optical output of the ICP 32 to the spectrometer 40, the preferred embodiment of the present invention employs Polymicro Technologies fiber optic bundle (Model PTA/LEI0019FF-030-ODP), consisting of 19 separate 200 micro µ core diameter fibers arranged in a round-to-linear bundle. The Acton Research Corporation 0.5 meter spectrometer (Model VM-505) equipped with a 2400 grooves/mm grading has been found suitable as the spectrometer. The optical radiation dispersed in the spectrometer is detected by a multichannel diode array detector 41. The EG&G Princeton Applied Research intensified diode array (Model 1420) and dime array controller print (Model 1463) are known to be suitable for this purpose. Preferably, the IEEE output of the detector 41 is connected to a personal computer 42 or workstation whereby the output of the spectrometer 40 can be stored, enhanced, processed, analyzed, and displayed.

Figures 2A, 2B:
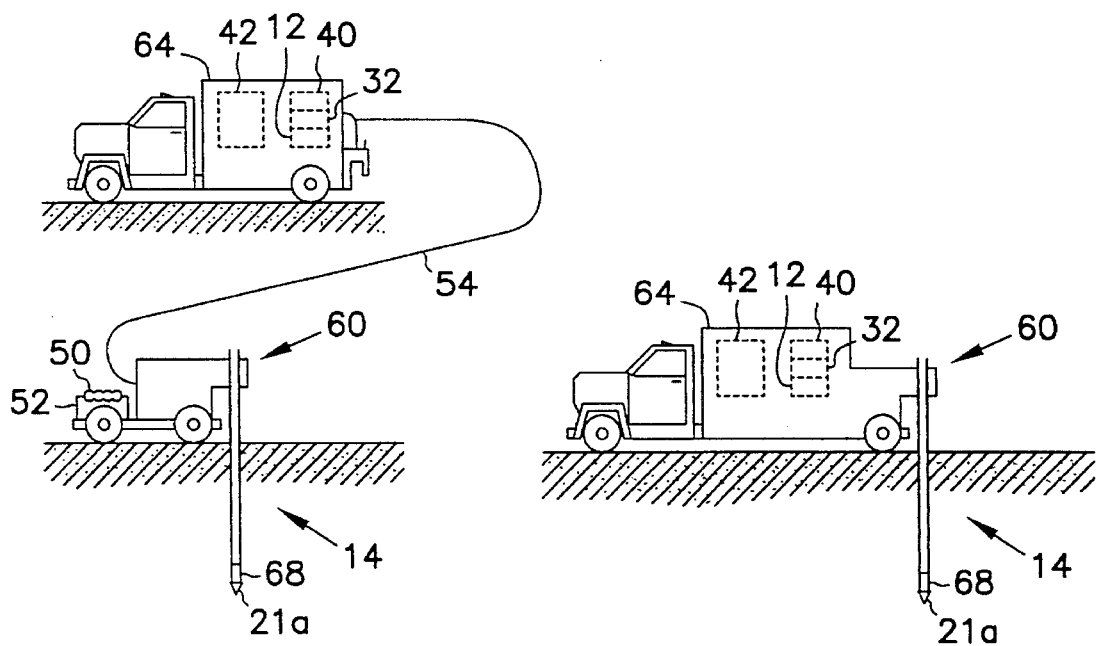
FIG. 2A illustrates an exemplary embodiment of a mobile inductively coupled plasma testing system for sampling subsurface formations.
FIG. 2B illustrates yet another exemplary embodiment of a mobile inductively coupled plasma testing system for sampling subsurface formation.

FIG. 2A illustrates one possible embodiment of a mobile inductively coupled plasma testing system according to the present invention. A hydraulic ram system 60 is trailered behind a truck 64. The truck 64 contains a power source for operating the components of the system. In use, the truck 64 may be positioned a distance from the toxic waste sampling site 14. The hydraulic ram system is positioned over the subsurface formation sought to be sampled. FIG. 2B illustrates another possible embodiment of a mobile inductively coupled plasma testing system wherein the hydraulic ram system 60 is mounted on the truck 64.

In the preferred embodiment, the aerosol robes 28 and 30 are 0.25 inch in diameter, made of Teflon™ or polyethylene material, and are pressurized to provide a gas flow of 1.0 liters/min. The argon 24 is held under pressure in the argon source 23 to provide pressure to the system. The preferred embodiment of the present invention is achieved transportation of material samples 25 and aerosol line 30 to a distance of 100 feet.

In the preferred embodiment of the present invention, the ICP source 32, the laser source 12 and spectrometer 40 are located in the truck 64. As explained above with respect to FIG. 1, an optical fiber 16 carries the laser beam from the laser 12 to the probe 20 while a second fiber 38 carries the output of the ICP 32 to the spectrometer 40. Using the equipment specified herein, the laser beam can be carried up to 30 meters on the fiber 16. Similarly, fiber 38 can carry, the output of the ICP 32 about 30 meters to the spectrometer 40.

Figure 3:
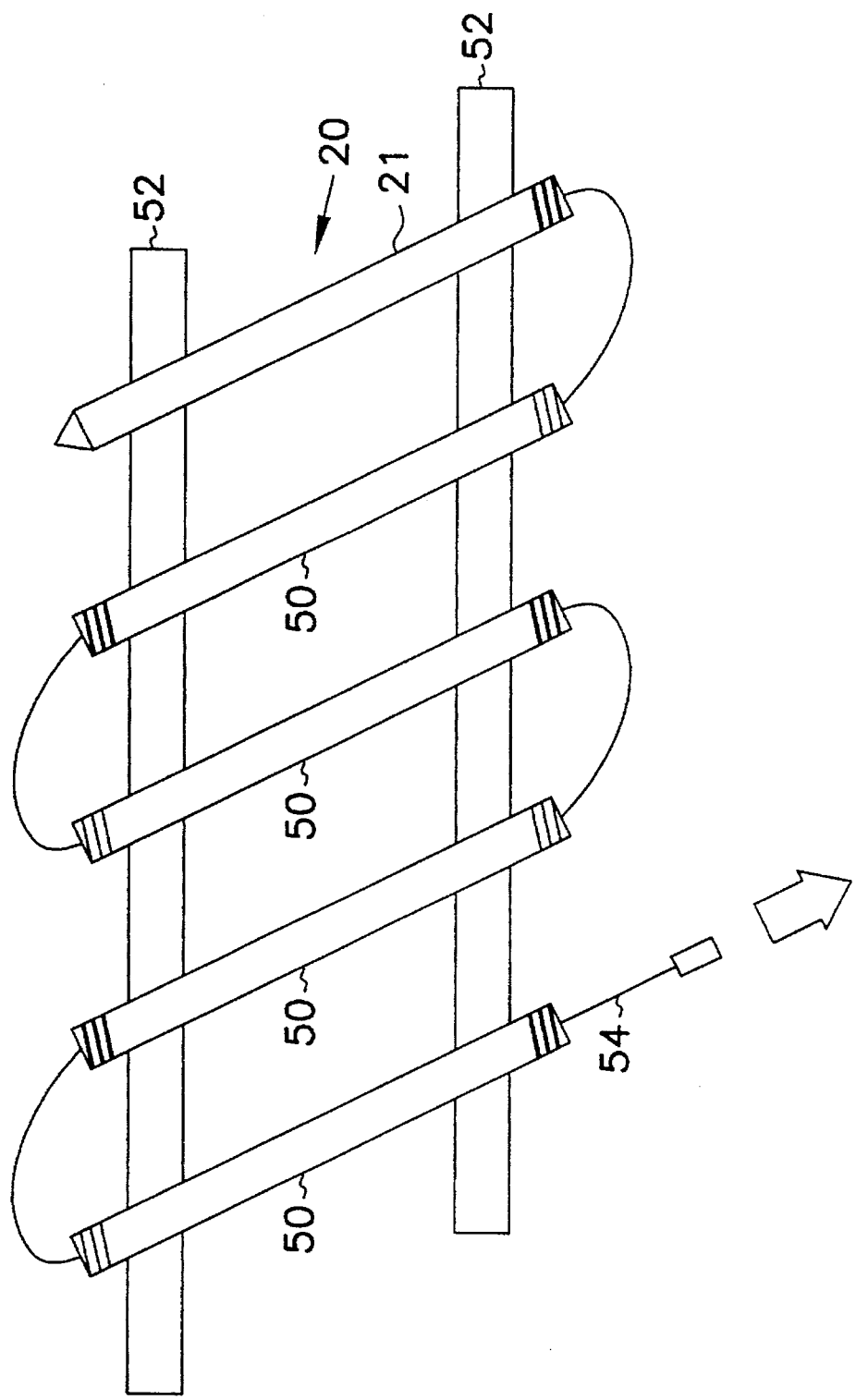
FIG. 3 is a simplified schematic diagram of the probe and corresponding tube sections according to the present invention.

The probe 20 is pushed into the earth using the hydraulic ram system 60. In the application shown in FIGS. 2A and 2B, an operator controls the hydraulic drive system to force the probe 20 into the subsurface formation. The tubes 28 and 30 and fiber 16, and other necessary electronic cables (not shown) are enclosed in a umbilical cord 54. As shown in FIG. 3, the probe 20 and other sections 50 of the push tube system are carded on a cradle 52. The upper portion of probe homing 21 and the ends of sections 50 are loosely threaded so that they can be assembled and disassembled, as the hydraulic drive system 60 pushes the probe 20 into the earth or pulls it out. Preferably, the hydraulic drive system 60 can be of the type used with the GeoProbe™ system available from GeoProbe™ Systems, Inc., or with other cone penetrometer systems.

Figure 4B:
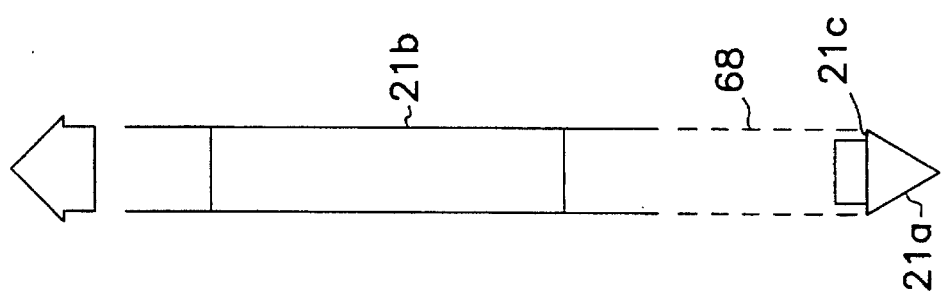
FIG. 4B is a simplified schematic diagram of a probe in its operative sampling position according to the present invention.
Figure 4A:
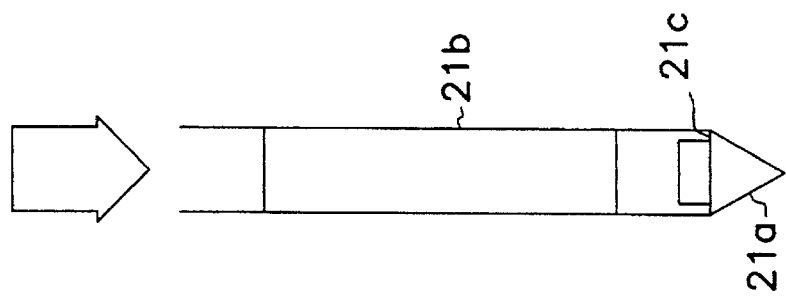
FIG. 4A is a simplified schematic diagram of a probe as configured for insertion into a subsurface formation according to the present invention.

FIG. 4A shows a simplified schematic diagram of the probe 20 in its configuration as it is pushed into the subsurface formation with the hydraulic system 60. Once the hydraulic ram has pressed the probe to its desired depth, its operation is reversed to pull the probe up a predetermined distance to expose a soil column 68. As shown in FIGS. 4A and 4B, the probe 20 includes a tip member 21a which is preferably interference fitted on the downwardly descending end of the homing 21b. Tip member 21a includes a barbed surface 21c which, when homing 21b is pulled upwardly from a position in a subsurface formation, causes the tip member 21a to separate from the homing 21b and remain stationary. When sampling is completed, the homing 21b of probe 20 is withdrawn from the down hole with the hydraulic ram. If any contamination has occurred, it is generally limited to the probe 20 or to the immediate accessories (i.e., cables, etc.), allowing relatively easy cleanup. Sample 25 itself is incinerated in the ICP plasma source 34. If necessary, the probe 20 and accessories can be disposed of and replaced at relatively low cost.

Figure 6:
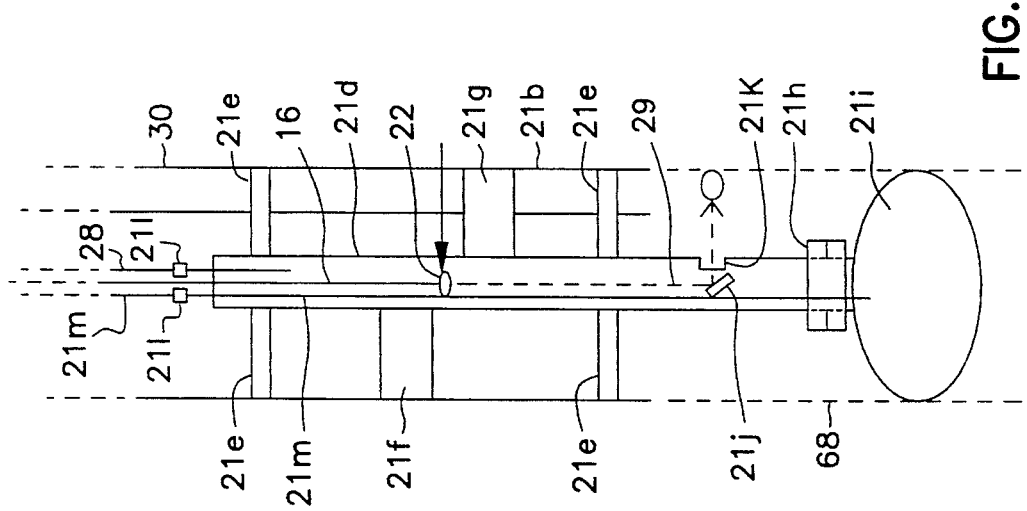
FIG. 6 is a more detailed schematic diagram of a probe according to the present invention deployed with the seal inflated in a position to collect a sample.

FIGS. 5A and 5B are simplified schematic diagrams of probe 20 illustrating its operation. FIG. 6 shows probe 20 in more detail in an operative position corresponding to FIG. 5B. In FIG. 5A, probe 20 is shown in its configuration just after it has been pushed to the desired depth and housing 21b has been withdrawn a predetermined distance, for example 6 to 12 inches, from its downward-most position. FIG. 5B and 6 illustrates the configuration of sampling probe 20 when in a sampling operation. Probe 20 includes an instrumentation tube 21d having an end portion from which an inflatable seal 21i is mounted using a rotary coupling 21h. Instrumentation tube 21d is rotatably mounted in homing 21b with sealed bearings 21e. Bearings 21 provide a seal between the instrumentation tube 21d and the housing 21b. An inflation robe 21m, connected to a source of pressurized gas on the sampling platform 60, extends through the instrumentation robe 21d and into the inflatable seal 21i. Also mounted in instrumentation tube 21d is a mirror 21j, which reflects laser radiation emitted from a fiber optic cable 16, which also extends down through instrumentation tube 21d and terminates at a position proximate optics 22. Optics 22 focus the laser radiation 29 from fiber 30 onto mirror (or prism) 21j, which reflects the energy onto the exposed soil column 68 through an opening 21k in the instrumentation tube 21d. A seal 21e provides a seal around instrumentation robe 21d so that when balloon seal 21i is inflated, a sealed ablation volume is created between the lower sealed bearing 21e and the inflated seal 21i. A gas line 28 delivers argon gas or other transport gas to the instrumentation tube 21d. Gas provided to the instrumentation tube sweeps down over the minor 21j, and through the opening 21k in the instrumentation tube. An aerosol sampling robe 30 extends down through housing 21b and seal 21e so that an aerosol borne sample of ablated material (carried on the medium delivered through line 28) may be extracted from the sampling probe and returned to the ICP 32 on the sampling platform 60. A pair of motors 21f and 21g are provided to raise and lower instrumentation tube 21d and to rotate the instrumentation robe about its longitudinal axis, respectively. Preferably, each of motors 21f and 21g engages instrumentation tube 21d with robber rollers, or with gear members, one mounted to the instrumentation tube 21d and the other rotated by the respective motor. Motors 21f and 21g are provided with control inputs to permit remote control from the surface, and in particular track 64.

Thus, once the probe is deployed in its operative position (after withdrawal of the housing 21b a predetermined distance from its downwardmost position) motor 21f is activated to lower instrumentation 21d to its sampling position, as shown in FIG. 5B. Next, seal 21i is inflated. Motor 21g is then used to rotate instrumentation robe 21d about its longitudinal axis while laser energy is applied to an area of the exposed soil column 68, to provide a rotational sweeping motion (up to 360 degrees) of the laser energy across the soil. Owing to the rotary couplings 21h and 21l, balloon 21i, robe 21m and robe or line 28, respectively, remain stationary while the instrumentation tube 21d rotates. The fiber 16 is allowed to flex and twist along its longitudinal axis with the rotation of the instrumentation tribe 21d. By moving the instrumentation robe incrementally up and down, fresh surfaces may be swept with the laser, allowing for multiple samples from one position of the homing 21b. A spiral sampling pattern can be achieved by rotating the instrumentation tube 21d while it is moved incrementally up or down.

Once all desired sampling has been completed, balloon seal 21i is deflated, the instrumentation tube 21d retracted into the housing 21b, and the probe 20 is either moved up to a higher elevation in the subsurface formation for further testing, or extracted from the subsurface formation altogether, in both cases leaving the tip member 21a behind. Thus, the invention allows that the down-hole can be tested at various depths by sequentially moving the probe 20 up to the depths at which testing is desired, and at each such depth deploying the instrumentation tube 21d for testing. In this manner, a profile of the soil column can be obtained. The probe 20 should not, however, be moved down after a test has been performed at a given level, since contamination of the probe may result.

Accordingly, the present invention provides a compact, simple and efficient means to obtain subsurface samples for analysis. The system avoids the need for large drill or insertion equipment. The invention can support organic sampling using out-gassed volatile material directly in the returning (Argon) stream. Laser energy or other thermal energy, for example hot gas, flash lamps, or sonic or ultrasonic sources also can be used to liberate the samples.

Although the invention has been described in its preferred form, those of skill in the art will recognize that many modifications made be made thereto without departing from the spirit and scope of the invention as defined in the claims appended hereto.

We claim:

1. A probe for use in sealing an ablation volume and obtaining a sample to be tested from a down-hole, comprising:

a cylindrical probe housing having a disengageable tip member mounted on a first end of the housing, so that when the probe is pulled upwardly in a down-hole, the tip member disengages from the first end of the housing and remains stationary in the down-hole, whereby a space between the tip member and the housing is created to expose a column of subsurface formation for sampling;

an instrumentation tube mounted in the housing for linear movement along its longitudinal axis;

a source of mechanical energy to move the instrumentation tube linearly along its longitudinal axis; and a seal member mounted on an end of the instrumentation tube disposed in the direction of the first end of the probe whereby the instrumentation tube can be extended from the housing and the seal member used to seal the down-hole to create an ablation volume.

2. A probe for use in obtaining a sample to be tested from a down-hole, comprising:

a cylindrical probe housing having a disengagable tip member;

an instrumentation tube mounted in the housing for rotational movement about its longitudinal axis and for linear movement along its axis;

an energy guide mounted to the instrumentation tube and directing energy from an energy source radially outward from the instrumentation tube;

a source of mechanical energy to rotate the instrumentation tube about its longitudinal axis;

a source of mechanical energy to move the instrumentation tube linearly along its longitudinal axis; and a seal member mounted on an end of the instrumentation tube disposed in the direction of the first end of the probe whereby the instrumentation tube can be extended from the housing and the seal member used to seal the down-hole to create an ablation volume, and whereby the instrumentation tube can be rotated about its axis to sweep the energy from the guide across a surface.

3. A probe according to claim 2 further including a rotary coupling for attaching the seal member to the instrumentation tube so that the instrumentation tube can rotate independently of the seal member.

4. A probe according to claim 2 further wherein the energy guide is a mirror or prism.

5. A probe according to claim 2 wherein there is a second seal member between the instrumentation tube and the housing so that there is an ablation volume created between the seal member and the second seal member.

6. A probe according to claim 2 further including a source of gas and an outlet for the gas connected to a gas conduit, so that the gas can be used to transport a sample from the instrumentation tube probe in the gas conduit to a remote location.

7. A method for obtaining a sample from a subsurface formation using a probe having a cylindrical probe housing and a disengagable tip member on a first end thereof comprising the steps of:

pushing the probe into the subsurface formation to a desired depth;

pulling the probe up from the desired depth and disengaging the tip member from the housing so that a column of the subsurface formation is exposed for sampling and an end of the housing is opened to permit deployment of sample gathering instrumentation; and obtaining a sample from the exposed column using instrumentation deployed from the housing through the opened end of the housing.

8. A method according to claim 7 further wherein the instrumentation is deployed in an instrumentation tube mounted in the housing for rotational movement about its longitudinal axis and for linear movement along its axis.

9. A method according to claim 8 further wherein there is an energy guide mounted to the instrumentation tube and directing energy from an energy source radially outward from the instrumentation tube.

10. A method according to claim 8 further wherein the probe includes a seal member mounted on an end of the instrumentation tube disposed in the direction of the opened end of the probe whereby the instrumentation tube can be extended from the housing and the seal member used to seal a down-hole to create an ablation volume, the instrumentation tube further mounted in the housing so that it can be rotated about its longitudinal axis to sweep energy from a guide across a surface.

11. A method according to claim 10 further wherein the probe includes a rotary coupling for attaching the seal member to the instrumentation tube so that the instrumentation tube can rotate independently of the seal member.

12. A method according to claim 11 further wherein the probe includes a second seal member between the instrumentation tube and the housing so that there is an ablation volume created in the exposed column of subsurface formation between the seal member mounted on an end of the instrumentation tube and the second seal member to allow sampling of an area of the exposed column of subsurface formation.

13. A method according to claim 7 further including the steps of raising the probe to a higher depth in the subsurface formation and repeating the deployment of the instrumentation tube whereby a profile of samples of the formation can be obtained.

* * * * *

UNITED STATES PATENT AND TRADEMARK OFFICE
CERTIFICATE OF CORRECTION

PATENT NO.    :   5,561,516

DATED         :   October 1, 1996

INVENTOR(S)   :   Donald T. Noble et al.

It is certified that error appears in the above-identified patent and that said Letters Patent is hereby corrected as shown below:

At Col. 3, line 14, please delete "The homing 21b" and insert --The housing 21b--.

At Col. 3, line 17, please delete "The homing 21b" and insert --The housing 21b--.

In the Abstract, line 6, please delete "soil point mad" and insert --soil point and--.

Signed and Sealed this

Thirteenth Day of January, 1998

Attest:

BRUCE LEHMAN

Attesting Officer

Commissioner of Patents and Trademarks